(12) United States Patent
Akahane et al.

(10) Patent No.: US 6,291,548 B1
(45) Date of Patent: Sep. 18, 2001

(54) DENTAL CEMENT COMPOSITION

(75) Inventors: Shoji Akahane; Hisashi Nakaseko, both of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/361,994

(22) Filed: Jul. 28, 1999

(30) Foreign Application Priority Data

Aug. 11, 1998 (JP) .................................................. 10-227197

(51) Int. Cl.$^7$ .............................. A61K 6/083; C08K 3/34; C08L 31/00
(52) U.S. Cl. ...................... 523/116; 523/117; 524/559; 524/832; 526/318.1; 526/326; 433/228.1; 260/998.11
(58) Field of Search .................................... 523/116, 117, 523/118; 524/559, 832; 526/318.1, 326; 260/998.11; 433/228.1

(56) References Cited

U.S. PATENT DOCUMENTS

| | | |
|---|---|---|
| 4,342,677 | 8/1982 | Muramatsu et al. . |
| 4,374,936 | 2/1983 | Tomioka et al. . |
| 4,524,824 | 6/1985 | Shimokobe et al. . |
| 4,591,384 | 5/1986 | Akahane et al. . |
| 4,632,824 | 12/1986 | Hirota et al. . |
| 4,647,600 | 3/1987 | Kawahara et al. . |
| 4,652,593 | 3/1987 | Kawahara et al. . |
| 4,678,436 | 7/1987 | Kondo et al. . |
| 4,775,592 | 10/1988 | Akahane et al. . |
| 4,900,697 | 2/1990 | Akahane et al. . |
| 5,063,257 | 11/1991 | Akahane et al. . |
| 5,171,763 * | 12/1992 | Ohno et al. .......................... 523/116 |
| 5,883,153 * | 3/1999 | Roberts et al. ....................... 523/116 |

* cited by examiner

Primary Examiner—Peter Szekely
(74) Attorney, Agent, or Firm—Oblon, Spivak, McClelland, Maier & Neustadt, P.C.

(57) ABSTRACT

A dental cement composition is disclosed, comprising a liquid material and a powder material, wherein said liquid material comprises 4-methacryloxyethyl trimellitic acid and water, said powder material comprising a powdered fluoroalumino silicate glass or a powdered metal oxide containing zinc oxide as the major component, the dental cement composition of the invention has a superior adhesive strength and adhesive durability to the tooth structure and superior in mechanical strengths, particularly in bending strength, without using dental adhesives requiring the surface treatment or priming.

12 Claims, No Drawings

DENTAL CEMENT COMPOSITION

BACKGROUND OF THE INVENTION

1. Field of the Invention

The present invention relates to a dental cement composition. More specifically, the invention relates to a dental cement composition utilizing an acid-base reaction between a 4-methacryloxyethyl trimellitic acid aqueous solution and a powdered fluoroalumino silicate glass or a powdered metal oxide containing zinc oxide as a major component.

2. Description of the Related Art

In the dental field, when an inlay, a crown, a bridge, or the like, are to be adhered zinc phosphate cements, carboxylate cements, glass ionomer cements, or resin cements have been widely used.

Of these cements, since the dental zinc phosphate cements have no adhesive properties to a tooth structure, have a low pH value due to the presence of phosphoric acid and may cause stimulation to the tooth structure at the initiation time of setting, the frequency of their use is being decreased.

Though the dental carboxyl ate cements are a dental cement having low stimulation to the tooth structure, they have a defect that the mechanical strength is low and lack in reliability.

The dental glass ionomer cements have adhesive properties to the tooth structure and have a anti-caries function from their properties to release fluorine, thus accordingly, the dental glass ionomer cements were now widely used. In addition, since set products obtained from a dental glass ionomer cement have translucent and are superior in esthetics, they can also be applied to filling. However, as compared with the dental resin cements, the dental glass ionomer cements are low in bending strengths and have brittleness, and therefore, they have clinically a defect that when used for filling on an occlusion surface of a posterior tooth, edge portions are liable to break off.

On the other hand, the dental resin cements are superior in mechanical strengths but an exclusive dental adhesive is necessary for the adhesion to the tooth structure, due to the fact that such cement have no adhesive properties to the tooth structure. Accordingly, the dental resin cements have a defect that complicated adhesion steps are required to obtain a thorough adhesive strength.

SUMMARY OF THE INVENTION

An object of the present invention is to provide a dental cement composition which overcomes the defects of the various dental cement compositions as described above, firmly adheres to a tooth structure without using dental adhesives requiring the surface treatment or priming, has superior adhesive durability, and is superior in mechanical strength, particularly in bending strength so that it is free from breaking off during filling on an occlusion surface of a posterior tooth.

In order to achieve the above-described problems, we, the present inventors made extensive and intensive investigations and paid an attention to the fact that 4-methacryloxyethyl trimellitic acid which has hitherto been used as a dental adhesive is a carboxylic acid group-containing acidic monomer. As a result of combining a 4-methacryloxyethyl trimellitic acid aqueous solution as a liquid material with a powder which has hitherto been used as a dental cement, it has been found that a dental cement composition which firmly adheres to a tooth structure, has superior adhesive durability and has superior mechanical strengths, particularly bending strength can be obtained, leading to accomplishment of the present invention.

That is, the dental cement composition according to the present invention comprises a liquid material and a powder material, wherein the liquid material comprises 4-methacryloxyethyl trimellitic acid and water, and the powder material comprises a powdered fluoroalumino silicate glass or a powdered metal oxide containing zinc oxide as the major component. Particularly when the liquid material is a 65% to 85% by weight aqueous solution of 4-methacryloxethyl trimellitic acid and, the liquid material and the powder material mixed in a weight ratio of from 1:0.5 to 1:4.0, remarkable superior properties can be obtained as compared with the conventional dental cement composition.

DETAILED DESCRIPTION OF THE INVENTION

4-Methacryloxyethyl trimellitic acid is a dentinal adhesive monomer which has hitherto been compounded in a dental adhesive or the like to impart adhesive properties to a tooth structure. Since this monomer is a carboxylic acid group-containing acidic monomer, it has such properties that it is rapidly set through an acid-base reaction in the presence of a powdered fluoroalumino silicate glass or a powdered metal oxide containing zinc oxide as the major component and water. For these reasons, as compared with polycarboxylic acids which have hitherto been used for dental glass ionomer cements, it can markedly improve the adhesive properties to a tooth structure so that a dental cement composition without using dental adhesives required the surface treatment or priming.

While this 4-methacryloxyethyl trimellitic acid causes an acid-base reaction with the powdered fluoroalumino silicate glass or the powdered metal oxide containing zinc oxide as a major component, since the 4-methacryloxyethyl trimellitic acid is a polymerizable monomer, it can be polymerized and set by itself. Thus, the dental cement composition according to the present invention can impart superior mechanical strengths, particularly bending strength as compared with the conventional dental cement compositions such as the dental glass ionomer cements.

In the present invention, by using the 4-methacryloxyethyl trimellitic acid in a state of an aqueous solution, its storage stability is improved. The 4-methacryloxyethyl trimellitic acid aqueous solution as the liquid material is preferably prepared in the amount of 15 to 35% by weight of water to 65 to 85% by weight of the 4-methacryloxyethyl trimellitic acid.

In the 4-methacryloxyethyl trimellitic acid aqueous solution, when the amount of the 4-methacryloxyethyl trimellitic acid is less than 65% by weight, the mechanical strengths, particularly bending strength of a set product is liable to be lowered. Further, when the amount of the 4-methacryloxyethyl trimellitic acid exceeds 85% by weight, the storage stability of the liquid material tends to be deteriorated.

The powder material to be mixed with the 4-methacryloxyethyl trimellitic acid aqueous solution as the liquid material causes an acid-base reaction in the presence of 4-methacryloxyethyl trimellitic acid and water, leading to setting. As the powder material, a powdered fluoroalumino silicate glass which is currently used as the powder component of the dental glass ionomer cement, or a powdered metal oxide containing zinc oxide as the major component, which is used as a powder component of the dental zinc phosphate cement or dental carboxylate cement, is preferable.

The powdered fluoroalumino silicate glass which is used in the dental glass ionomer cement as referred to herein is preferably a powdered fluoroalumino silicate glass containing $Al^{3+}$, $Si^{4+}$, $F^-$, and $O^{2-}$ as the major components and additionally containing $Sr^{2+}$ and/or $Ca^{2+}$. Further, the proportions of $Al^{3+}$, $Si^{4+}$, $F^-$, and the sum of $Sr^{2+}$. Further, the preferably from 10 to 21% by weight, from 9 to 24% by weight, from 1 to 20% by weight, and from 10 to 34% by weight, respectively based on the total weight of the glass.

These proportions of the major components greatly influence the handling property and physical properties such as setting rate, final strength, and solubility. When the proportion of $Al^{3+}$ is less than 10% by weight, the setting rate is slow, and the strength tends to be lowered. When the proportion of $Al^{3+}$ exceeds 21% by weight, the preparation of the glass is difficult, and the transparency is lowered, whereby the esthetics are liable to be inferior. When the proportion of $Si^{4+}$ is less than 9% by weight, the preparation of the glass is liable to be difficult, too. When the proportion of $Si^{4+}$ exceeds 24% by weight, the setting rate is liable to be slow, and the strength is low, so that a problem in durability is liable to occur. When the proportion of $F^-$ is less than 1% by weight, the working time during mixing of the dental cement is short, so that the handling for use is liable to be difficult. When the proportion of $F^-$ exceeds 20% by weight, the final setting time is long, and the solubility in water is high, so that the durability is liable to be inferior. When the proportion of the sum of $Sr^{2+}$ and $Ca^{2+}$ is less than 10% by weight, the setting sharpness can not exhibit, and the setting time is liable to be long. Further, in this case, the preparation of the glass is liable to be difficult. When the proportion of the sum of $Sr^{2+}$ and $Ca^{2+}$ exceeds 34% by weight, the working time is short, and the setting rate is too fast, so that the actual use is liable to be difficult. In this case, the solubility in water is so high that the durability is liable to be lowered. The fluoroalumino silicate glass used in the present invention can be prepared by the known preparation methods of glass.

The powdered metal oxide containing zinc oxide as the major component as referred to herein is represented by a powder of a dental zinc phosphate cement or a powder of a dental carboxylate cement. Generally, these powders can be prepared by 70 to 90% by weight of zinc oxide which is mixed with 10 to 30% by weight of a metal oxide such as magnesium oxide, then sintering the mixture at a high temperature of 700° C. or higher, cooling the sintered product, and grinding in a ball mill or the like. Examples of other metal oxides which can be used in the present invention include metal oxides such as strontium oxide, silicon dioxide, ferric oxide, and yttrium oxide. These metal oxides other than zinc oxide function as a promoter to promote the reaction with 4-methacryloxyethyl trimellitic acid.

The powdered fluoroalumino silicate glass or powdered metal oxide containing zinc oxide as the major component, which is used as the powder material, is desirably adjusted in terms of the particle size and preferably has a mean particle size of from 0.02 $\mu$m to 10 $\mu$m, and more preferably from 0.02 $\mu$m to 5 $\mu$m. In case where a fine powder having a mean particle size of less than 0.02 $\mu$m, the reaction with 4-methacryloxyethyl trimellitic acid is too fast, so that the handling property is liable to be deteriorated. In case where the mean particle size exceeds 10 $\mu$m, the setting rate is too slow, and the smoothness of the set dental cement composition surface is liable to be deteriorated. In addition, as the powder material which is used in the dental cement composition according to the present invention, those obtained surface treatment by a silane coupling agent in the usual manner can also be used.

A suitable mixing proportion of the liquid material of the 4-methacryloxyethyl trimellitic acid and the powder material of the powdered fluoroalumino silicate glass or the powdered metal oxide containing zinc oxide as the major component is such that the powder material is used in a proportion of 0.5 to 4.0 parts by weight based on 1 part by weight of the liquid material. From the points of view of the mixing handling property and the setting mechanism, it is preferred that the powder material is used in a proportion of 1.5 to 3.0 parts by weight based on 1 part by weight of the liquid material.

When the mixing proportion of the powder material exceeds 4.0 parts by weight, the mixing of the 4-methacryloxyethyl trimellitic acid aqueous solution with the powdered fluoroalumino silicate glass or the powdered metal oxide containing zinc oxide as the major component is difficult, so that the adhesive properties to the tooth structure are liable to be inferior. When the mixing proportion of the powder material is less than 0.5 parts by weight, the mechanical strength of the set dental cement composition are liable to be lowered. In the dental cement composition according to the present invention, usually used polymerization catalysts, polymerization inhibitors, ultraviolet light absorbers, coloring agents, thickeners, etc. can be added, if desired.

As the polymerization catalysts which are optionally used in the dental cement composition according to the present invention, polymerization catalysts usually used such as sodium p-toluenesulfinate, ascorbic acid, phenylglycine, and sodium benzenesulfinate can be used. As the polymerization inhibitors, conventional polymerization inhibitors such as dibutylhydroxytoluene and hydroquinone can be used. As the ultraviolet light absorbers, conventional ultraviolet light absorbers such as 2-(2'-hydroxy-5'-methylphenyl) benzotriazole can be used. Polymerization catalysts, polymerization inhibitors, coloring agents, and the like are preferably compounded in powder materials. The ultraviolet light absorbers and thickeners are preferably compounded in the liquid material.

The dental cement composition according to the present invention has a superior adhesive strength and adhesive durability and is superior in mechanical strengths, particularly bending strength, without using dental adhesives requiring the surface treatment or priming. In addition, since the set product is translucent, the dental cement composition according to the present invention can be used for various applications such as not only cementing of dental prostheses made of dental metals, dental ceramics, etc. but also dentinal adhesive materials for filling materials such as dental composite resins, pit and fissure sealants of an occlusion surface, etc., lining materials of a cavity, adhesive materials for an orthodontic bracket, and the like.

The dental cement composition according to the present invention is described in more detail with reference to the following Examples.

Preparation of Powdered Fluoroalumino Silicate Glass as Powder Material (1) Powdered Fluoroalumino Silicate Glass I 21 grams of aluminum oxide, 44 g of anhydrous silicic acid, 12 g of calcium fluoride, 14 g of calcium phosphate, and 9 g of strontium carbonate were thoroughly mixed, and the mixture was kept in a high-temperature electric furnace at a 1,200° C. for 5 hours, thereby melting a glass. After melting, the glass was cooled and ground in a ball mill for 10 hours. The ground glass was passed through a 200-mesh (ASTM) sieve, and the resulting powder material was taken as a powdered fluoroalumino silicate glass I.

(2) Powdered Fluoroalumino Silicate Glass II 23 grams of aluminum oxide, 41 g of anhydrous silicic acid, 10 g of calcium fluoride, 13 g of calcium phosphate, and 13 g of aluminum phosphate were thoroughly mixed, and the mixture was kept in a high-temperature electric furnace at a 1,100° C. for 5 hours, thereby melting a glass. After melting, the glass was cooled and ground in a ball mill for 10 hours. The ground glass was passed through a 200-mesh (ASTM) sieve, and the resulting powder material was taken as a powdered fluoroalumino silicate glass II.

(3) Powdered Fluoroalumino Silicate Glass III 22 grams of aluminum oxide, 43 g of anhydrous silicic acid, 12 g of calcium fluoride, 15 g of calcium phosphate, and 8 g of strontium carbonate were thoroughly mixed, and the mixture was kept in a high-temperature electric furnace at a 1,200° C. for 5 hours, thereby melting a glass. After melting, the glass was cooled and ground in a ball mill for 10 hours. The ground glass was passed through a 200-mesh (ASTM) sieve, and 100 parts by weight of the resulting powder material was added by 1 part by weight of sodium p-toluenesulfinate to prepare a powder, which was taken as a powdered fluoroalumino silicate glass III.

Preparation of Powdered Metal Oxide Containing Zinc Oxide as Major Component as Powder Material (1) Powdered Metal Oxide I Containing Zinc Oxide as Major Component 88 grams of zinc oxide and 12 g of magnesium oxide were thoroughly mixed, and the mixture was kept in a high-temperature electric furnace at 1,000° C. for 5 hours, thereby sintering it. After sintering, the sintered product was cooled and ground in a ball mill for 10 hours. The ground product was passed through a 200-mesh (ASTM) sieve, and the resulting powder material was taken as a powdered metal oxide I containing zinc oxide as the major component.

(2) Powdered Metal Oxide II Containing Zinc Oxide as Major Component 80 of zinc oxide, 18 g of magnesium oxide, and 2 g of strontium oxide were thoroughly mixed, and the mixture was kept in a high-temperature electric furnace at 900° C. for 5 hours, thereby sintering it. After sintering, the sintered product was cooled and ground in a ball mill for 10 hours. The ground product was passed through a 200-mesh (ASTM) sieve, and the resulting powder material was taken as a powdered metal oxide II containing zinc oxide as the major component.

Adhesive Strength and Adhesive Durability Tests

A surface of fresh bovine anterior teeth was polished with a waterproof paper #600 while pouring water, and 40 enamels and 40 dentins were exposed to obtain surfaces to be adhered. An adhesion area was defined using an aluminum-made masking tape having an opening with a diameter of 3 mm. Thereafter, the mixed dental cement composition was placed on the surface to be adhered, and a stainless steel-made columnar rod, the surface of which had been previously polished with a waterproof paper #600, brought into press contact therewith by hand. The assembly was allowed to stand in a chamber at 37° C. and at a relative humidity of 100% for one hour and immersed in water at 37° C. for 23 hours.

Thereafter, 20 of the 40 specimens were measured for the adhesive strength by means of a universal testing machine (a product name: Autograph, manufactured by Shimadzu Corporation) at a cross-head speed of 1.0 mm/min.

The remaining 20 specimens were subjected to a thermal cycle test, in which a stress due to the temperature difference was continuously given 1,000 times at an interval of 30 seconds in a method for alternately dipping in cold water at 5° C. and warm water at 55° C. using a thermal cycle testing apparatus (manufactured by Thomas Science Instruments), and then measured for the adhesive strength by means of a universal testing machine (a product name: Autograph, manufactured by Shimadzu Corporation) at a cross-head speed of 1.0 mm/min. This test was taken as the adhesive durability test. The results were shown in terms of an average value of the respective 20 specimens. [Bending Strength Test]

The mixed dental cement composition was filled in an acrylic resin-made tube having an inside diameter of 3 mm and a length of 25 mm and brought into press contact with a glass sheet via cellophane, to obtain 30 columnar set products. The obtained specimens were immersed in distilled water at 37° C. for 24 hours and subjected to a three-point bending test by means of a universal testing machine (a product name: Autograph, manufactured by Shimadzu Corporation) at a cross-head speed of 1.0 mm/min. and at a span of 20 mm. The results were shown in terms of an average value of the respective 30 specimens.

EXAMPLE 1

4-Methacryloxyethyl trimellitic acid (7.5 g) and distilled water (2.5 g) were weighed and mixed at room temperature for 4 hours to prepare a liquid material. The liquid material (1.0 g) and the powdered fluoroalumino silicate glass I (1.0 g) as the powder material were weighed on a mixing paper and mixed for 40 seconds using a spatula, thereby uniformly mixing the liquid material and the powder material. The working time was 3 minutes at room temperature of 23° C.

The results of the adhesive strength and adhesive durability tests and the bending strength test of the dental cement are shown in Table 1.

EXAMPLE 2

4-Methacryloxyethyl trimellitic acid (8.0 g) and distilled water (2.0 g) were weighed and mixed at room temperature for 4 hours to prepare a liquid material. The liquid material (1.0 g) and the powdered fluoroalumino silicate glass II (2.0 g) as the powder material were weighed on a mixing paper and mixed in the same manner as in Example 1 using a spatula, thereby uniformly mixing the liquid material and the powder material. The working time was 2 minutes and 30 seconds at room temperature of 23° C.

The results of the adhesive strength and adhesive durability tests and the bending strength test of the dental cement are shown in Table 1.

EXAMPLE 3

4-Methacryloxyethyl trimellitic acid (6.7 g) and distilled water (3.3 g) were weighed and mixed at room temperature for 4 hours to prepare a liquid material. The liquid material (1.0 g) and the powdered fluoroalumino silicate glass I (3.5 g) as the powder material were weighed on a mixing paper and mixed in the same manner as in Example 1 using a spatula, thereby uniformly mixing the liquid material and the powder material. The working time was 2 minutes at room temperature of 23° C.

The results of the adhesive strength and adhesive durability tests and the bending strength test of the dental cement are shown in Table 1.

EXAMPLE 4

4-Methacryloxyethyl trimellitic acid (8.4 g) and distilled water (1.6 g) were weighed and mixed at room temperature for 4 hours to prepare a liquid material. The liquid material (1.0 g) and the powdered fluoroalumino silicate glass III (3.0 g) as the powder material were weighed on a mixing paper and mixed in the same manner as in Example 1 using a spatula, thereby uniformly mixing the liquid material and the powder material. The working time was 2 minutes and 10 seconds at room temperature of 23° C.

The results of the adhesive strength and adhesive durability tests and the bending strength test of the dental cement are shown in Table 1.

EXAMPLE 5

4-Methacryloxyethyl trimellitic acid (8.2 g) and distilled water (1.8 g) were weighed and mixed at room temperature for 4 hours to prepare a liquid material. The liquid material (1.0 g) and the powdered metal oxide I (1.5 g) containing zinc oxide as the major component as the powder material were weighed on a mixing paper and mixed in the same manner as in Example 1 using a spatula, thereby uniformly mixing the liquid material and the powder material. The working time was 2 minutes and 45 seconds at room temperature of 23° C.

The results of the adhesive strength and adhesive durability tests and the bending strength test of the dental cement are shown in Table 1.

EXAMPLE 6

4-Methacryloxyethyl trimellitic acid (7.2 g) and distilled water (2.8 g) were weighed and mixed at room temperature for 4 hours to prepare a liquid material. The liquid material (1.0 g) and the powdered metal oxide II (3.7 g) containing zinc oxide as the major component as the powder material were weighed on a mixing paper and mixed in the same manner as in Example 1 using a spatula, thereby uniformly mixing the liquid material and the powder material. The working time was 2 minutes at room temperature of 23° C.

The results of the adhesive strength and adhesive durability tests and the bending strength test of the dental cement are shown in Table 1.

Comparative Example 1

"Fuji I" (a product of GC Corporation) was used as the conventional dental glass ionomer cement. The cement liquid material (1.0 g) and the cement powder material (1.8 g) were weighed on a mixing paper and mixed in the same manner as in Example 1 using a spatula, thereby uniformly mixing the liquid material and the powder material. The working time was 2 minutes at room temperature of 23° C.

The results of the adhesive strength and adhesive durability tests and the bending strength test of the dental glass ionomer cement are shown in Table 1.

Comparative Example 2

"LIVCARBO" (a product of GC Corporation) was used as the conventional dental carboxylate cement. The cement liquid material (1.0 g) and the cement powder material (2.0 g) were weighed on a mixing paper and mixed in the same manner as in Example 1 using a spatula, thereby uniformly mixing the liquid material and the powder material. The working time was 3 minutes at room temperature of 23° C.

The results of the adhesive strength and adhesive durability tests and the bending strength test of the dental carboxylate cement are shown in Table 1.

TABLE 1

|  | Adhesive strength (MPa) | | Adhesive strength after thermal cycle test (MPa) | | Bending strength | |
| --- | --- | --- | --- | --- | --- | --- |
|  | Enamel | Dentin | Enamel | Dentin | (MPa) | Working time |
| Example 1 | 7.7 ± 2.5 | 6.1 ± 2.5 | 7.5 ± 2.4 | 6.2 ± 2.0 | 31 ± 2.0 | 3 min. |
| Example 2 | 8.5 ± 2.9 | 6.5 ± 2.4 | 8.2 ± 2.4 | 6.1 ± 2.6 | 36 ± 2.5 | 2 min. 30 sec. |
| Example 3 | 6.9 ± 2.2 | 5.5 ± 2.0 | 7.5 ± 2.1 | 6.1 ± 2.5 | 45 ± 2.5 | 2 min. |
| Example 4 | 7.7 ± 2.5 | 6.0 ± 2.1 | 8.3 ± 2.3 | 6.0 ± 2.5 | 55 ± 1.8 | 2 min. 10 sec. |
| Example 5 | 6.5 ± 2.6 | 5.8 ± 2.4 | 6.7 ± 2.0 | 6.1 ± 2.2 | 30 ± 2.0 | 2 min. 45 sec. |
| Example 6 | 8.4 ± 2.3 | 6.7 ± 2.2 | 8.5 ± 2.5 | 6.4 ± 2.1 | 42 ± 2.3 | 2 min. |
| Comparative Example 1 | 4.2 ± 3.3 | 4.7 ± 3.5 | 2.0 ± 1.6 | 1.4 ± 1.0 | 11 ± 1.1 | 2 min. |
| Comparative Example 2 | 3.3 ± 2.5 | 2.9 ± 2.0 | 1.2 ± 0.7 | 0.8 ± 0.7 | 5.0 ± 0.7 | 3 min. |

As is clear from the foregoing Examples and Comparative Examples, the dental cement composition according to the present invention is a dental cement composition which is free from breaking off during filling on an occlusion surface of a posterior tooth since it has a superior adhesive strength and adhesive durability to the tooth structure and is superior in mechanical strengths, particularly bending strength, without using dental adhesives requiring the surface treatment or priming. Therefore, it is of great value to contributing to the dental remedy.

While the invention has been described in detail and with reference to specific embodiments thereof, it will be apparent to one skilled in the art that various changes and modifications can be made therein without departing from the spirit and scope thereof.

What is claimed is:

1. A dental cement composition, comprising a liquid material and a powder material, wherein said liquid material is a 65–85% by weight aqueous solution of 4-methacryloxyethyl trimellitic acid, and said powder material comprises a powdered fluoroalumino silicate glass or a powdered metal oxide containing zinc oxide as a major component, said liquid material and said powder material being mixed in a weight ratio of from 1:0.5 to 1:4.0.

2. The dental cement composition of claim 1, wherein said powdered flouroalumino silicate glass is a powdered flouroalumino silicate glass containing $Al^{3+}$, $Si^{4+}$, $F^-$ and $O^{2-}$ as the major components and additionally containing $Sr^{2+}$ $Ca^{2+}$ or both.

3. The dental cement composition of claim 1, wherein said powdered metal oxide containing zinc oxide as a major component further comprises a metal oxide other than zinc oxide, which is selected from the group consisting of magnesium oxide, strontium oxide, silicon dioxide, ferric oxide, and yttrium oxide.

4. The dental cement composition of claim 1, wherein said powdered material is a powder material having a mean particle size of 0.02 μm to 10 μm.

5. The dental cement composition of claim 1, wherein said powdered material is a powder material containing a polymerization catalyst.

6. The dental cement composition of claim 2, wherein the content of $Al^{3+}$ is from 10 to 21% by weight.

7. The dental cement composition of claim 2, wherein the content of $Si^{4+}$ is from 9 to 24% by weight.

8. The dental cement composition of claim 2, wherein the content of $F^-$ is from 1 to 20% by weight.

9. The dental cement composition of claim 2, wherein the sum of $Sr^{2+}$ and $Ca^{2+}$ is from 10 to 34% by weight.

10. A method of providing adhesive properties to a tooth structure, which comprises applying an effective amount of the dental cement composition of claim 1, to said tooth structure.

11. The method of claim 10, wherein said tooth structure comprises enamel.

12. The method of claim 10, wherein said tooth structure comprises dentin.

* * * * *